(12) United States Patent
Bosman et al.

(10) Patent No.: US 8,827,947 B2
(45) Date of Patent: Sep. 9, 2014

(54) BREAST PUMP

(75) Inventors: Franciscus Jozef Bosman, Eindhoven (NL); Bernardo Arnoldus Mulder, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 5 days.

(21) Appl. No.: 13/810,747

(22) PCT Filed: Jul. 14, 2011

(86) PCT No.: PCT/IB2011/053140
§ 371 (c)(1),
(2), (4) Date: Jan. 17, 2013

(87) PCT Pub. No.: WO2012/014113
PCT Pub. Date: Feb. 2, 2012

(65) Prior Publication Data
US 2013/0123688 A1   May 16, 2013

(30) Foreign Application Priority Data

Jul. 27, 2010 (EP) .................................. 10170866

(51) Int. Cl.
*A61M 1/06* (2006.01)
*A61M 1/00* (2006.01)

(52) U.S. Cl.
CPC .............. *A61M 1/06* (2013.01); *A61M 1/0037* (2013.01); *A61M 1/0068* (2013.01)
USPC ...................................................... 604/74

(58) Field of Classification Search
CPC ............ A61M 1/06; A61M 2001/064; A61M 2001/0072; A61M 2205/075; A61M 1/0031; A61M 2001/066; A61M 1/0049; A61M 2001/0068; A61M 1/0037; A61M 2205/073; A01J 5/06

USPC ................................................... 604/74, 119
See application file for complete search history.

(56) References Cited

U.S. PATENT DOCUMENTS

| 4,323,067 A | 4/1982 | Adams |
| 5,358,476 A | 10/1994 | Wilson |
| 5,749,850 A | 5/1998 | Williams et al. |
| 5,947,923 A | 9/1999 | Uehara et al. |
| 7,008,400 B2 * | 3/2006 | Silver et al. ..................... 604/74 |
| 2001/0038799 A1 | 11/2001 | Silver et al. |
| 2005/0154349 A1 | 7/2005 | Renz et al. |
| 2007/0088250 A1 | 4/2007 | Silver et al. |

FOREIGN PATENT DOCUMENTS

| CN | 201290924 Y | 8/2009 |
| WO | 2004058330 A1 | 7/2004 |
| WO | 2005067997 A1 | 7/2005 |

* cited by examiner

*Primary Examiner* — Nicholas Lucchesi
*Assistant Examiner* — Diva K Chander

(57) ABSTRACT

In a breast pump, milk expressed from a user's nipple may be drawn into the pumping mechanism used to create a vacuum. This can lead to unhygienic situations because pumping mechanisms are difficult or impossible to clean by a user. The present invention relates to a breast pump comprising first and second pressure chambers (22, 23) and an actuator (20) disposed to fluidly divide the two chambers (22, 23). The actuator (20) is movable to generate an inverse pressure differential in the second chamber (23) when a pressure differential is generated in the first pressure chamber (22), or a pressure differential is released from the first pressure chamber (22). Furthermore, the actuator (20) comprises a first piston element (30) and a second piston element (32), and wherein the first pressure chamber (22) is disposed between the first piston element (30) and the second piston element (32).

10 Claims, 5 Drawing Sheets

BREAST PUMP

FIELD OF THE INVENTION

The present invention relates to a breast pump for extracting milk from a breast of a user.

BACKGROUND OF THE INVENTION

Breast pumps are well known devices for extracting milk from a breast of a user. A breast pump may be used if the baby or infant is not itself able to express milk from the breast, or if the mother is separated from the baby or infant, for example, if away from the baby at work. The use of a breast pump to express milk may also be used to stimulate and increase milk production in women with a low milk supply.

Breast pumps make use of a vacuum to induce milk expression from a nursing mother's breast. The pumping action of the device draws the milk from the nipple to a collection vessel, and the pressure and/or frequency may generally be adjusted to the preferences of the mother.

WO 2004/058330 discloses a manual breast pump comprising a breast cup, a pump housing with a piston and an activation mechanism in the form of a handle, together with a container for collection of the milk. The breast cup comprises a preferably rigid outer part and an inner, preferably completely or partially flexible, part, where two mutually separate chambers are provided between the outer part and the inner part. The piston comprises a membrane that connects the periphery of the piston with the wall of the pump housing and thereby divides the pump housing into an upper chamber and a lower chamber, wherein said upper chamber is in fluid contact with the chambers of the breast cup with the help of two openings with associated tubes, and the lower chamber is in fluid contact with the inside of the breast cup.

A general embodiment of a known breast pump for extracting milk from a user's breast is shown in FIG. 1. Such a breast pump 1 comprises a main body 2 and a collection vessel 3, such as a feeding bottle or bag. The collection vessel 3 is attached to the main body 2 by a screw fitting.

A breast-receiving funnel 5 extends from the main body 2 for receiving the breast of a user. The funnel 5 has an inner surface 6 and comprises a mouth 7 and a throat 8. The mouth 7 is open at an outer end and the inner surface 6 of the funnel 5 converges from the outer end towards the throat 8 to form a hollow recess in which a breast is received.

A vacuum pump unit 9 is fluidly connected to the main body 2 or is formed in the main body 2 to create a vacuum, and is generally operated by means of a user manually operating a handle 4 or by means of an electric motor actuating the vacuum pump.

However, a problem with the above described breast pump arrangement is that a negative pressure is generally generated at the breast to encourage milk expression by the pump unit producing a negative pressure below the atmospheric pressure. Therefore, it is known for milk to be drawn into the pumping mechanism. This can lead to unhygienic situations because pumping mechanisms are difficult or impossible to clean by a user.

It is also known to provide breast pumps with an insert which provides active massaging or kneading of the breast and/or nipple during milk extraction, to improve the rate of milk extraction and the comfort of the user. However, such an operation requires generation of a positive pressure in the insert and so a separate pump is required to generate such a pressure profile.

SUMMARY OF THE INVENTION

Therefore, it is an object of the invention to provide a breast pump which substantially alleviates or overcomes the problems mentioned above.

According to the present invention, there is provided a breast pump comprising a first pressure chamber, a second pressure chamber and an actuator disposed to fluidly divide the two chambers, wherein the actuator is movable to generate an inverse pressure differential in the second chamber when a pressure differential is generated in the first pressure chamber, or a pressure differential is released from the first pressure chamber, wherein the actuator comprises a first piston element and a second piston element, and wherein the first pressure chamber is disposed between the first piston element and the second piston element.

The breast pump may further comprise a breast receiving funnel, wherein the second pressure chamber includes a breast receiving recess defined by the funnel.

Conveniently, the breast pump further comprises a compartment, wherein the actuator is slidably disposed in the compartment.

The first and second piston elements may each comprise a seal extending from an outer rim of each piston element to an inner surface of the compartment to form a fluid seal. Preferably, the seal is a rolling seal.

Advantageously, the first pressure chamber is disposed between the seal of the first piston element and the seal of the second piston element.

Conveniently, the second pressure chamber extends from the seal of the second piston element.

The second piston element may extend from the first piston element.

Advantageously, the diameter of the first piston element is greater than the diameter of the second piston element.

Advantageously, the breast pump further comprises an inflatable insert disposed in the breast receiving funnel for massaging a user's breast disposed therein, and a pressure conduit which fluidly communicates the insert with the first pressure chamber, such that the insert inflates when a positive pressure differential is generated in the first pressure chamber.

The breast pump may further comprise a pump unit for generating a pressure differential in the first pressure chamber.

Preferably, the pump unit generates a pressure differential in the first pressure chamber.

BRIEF DESCRIPTION OF THE DRAWINGS

Preferred embodiments of the invention will now be described, by way of example only, with reference to the accompanying drawings, in which.

DETAILED DESCRIPTION OF THE EMBODIMENTS

Figure 1:
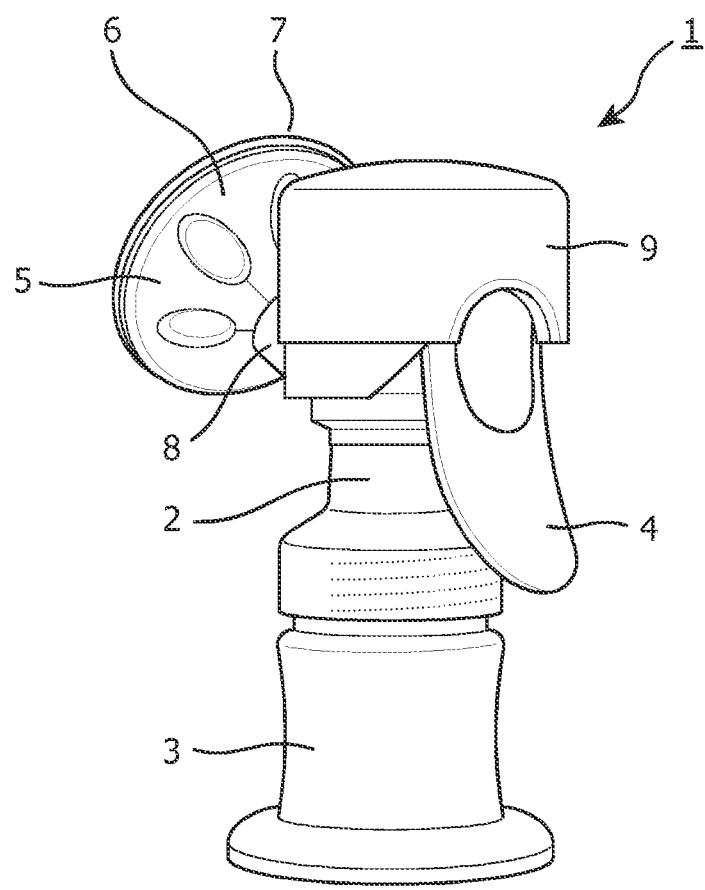
FIG. 1 shows a schematic cross-sectional view of an existing breast pump.
Figure 2:
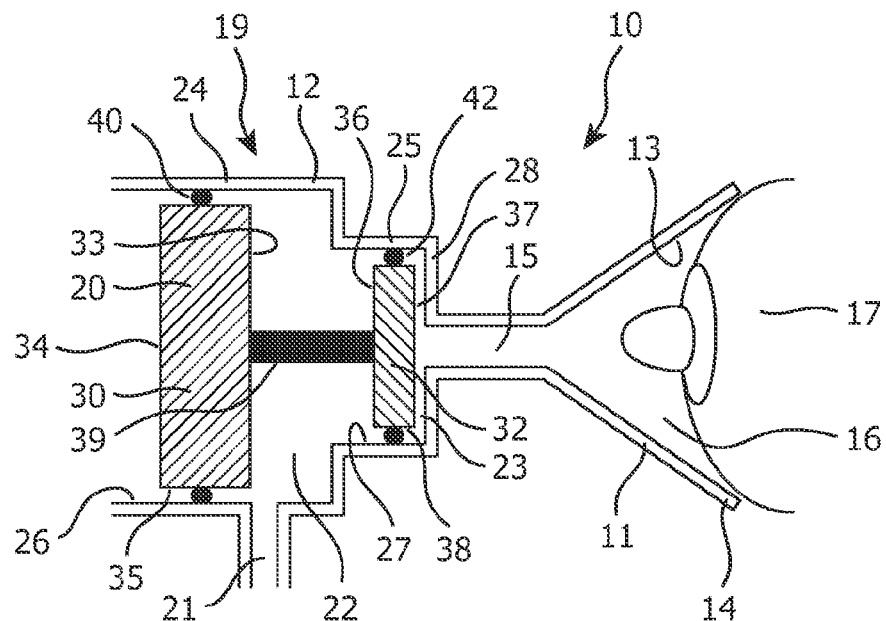
FIG. 2 shows a schematic cross-sectional view of a first embodiment of a breast pump with an actuator in a neutral position.
Figure 3:
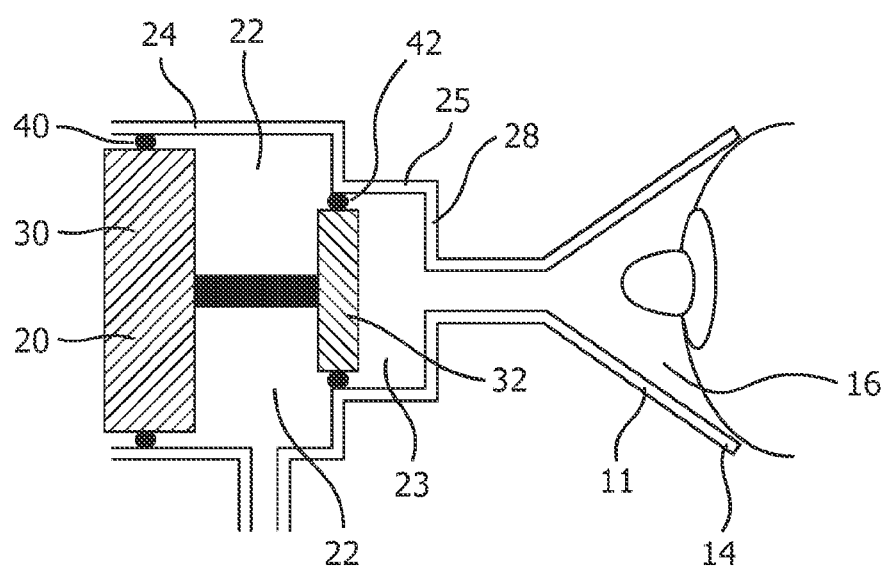
FIG. 3 shows a schematic cross-sectional view of the breast pump shown in FIG. 2 with an actuator in a retracted position.

Referring now to FIGS. 2 and 3, part of a breast pump 10 is schematically shown comprising a breast receiving funnel 11 and a main body 12. A milk receiving vessel (not shown) is attached to the main body and is a feeding bottle for an infant or baby; however it will be appreciated that the vessel may alternatively be a bag or other known container. The breast receiving funnel 11, main body 12 and milk receiving vessel (not shown) are formed from a rigid, non-deformable material, such as a rigid plastic, for ease of manufacture and to allow sterilization, although alternative suitable materials may be used.

The funnel 11 extends from the main body 12 of the breast pump 10 and is integrally formed therewith. The funnel 11 has an inner surface 13 extending between a mouth 14 and a throat 15 of the funnel 11. The mouth 14 is open at an outer end and converges toward the throat 15 to form a breast receiving recess 16 in which a user's breast 17 is received. The throat 15 of the funnel 11 extends from the main body 12 such that a fluid passageway is formed from the breast receiving recess 16, through the main body 12 to the milk receiving vessel (not shown) to allow milk expressed from a user's breast 17 to flow to the milk receiving vessel (not shown).

A compartment 19 is formed in the main body 12 and an actuator 20 is disposed therein. The actuator 20 divides the compartment 19 into a first pressure chamber 22 and a second pressure chamber 23. An inlet 21 extends from the first pressure chamber 22 and fluidly connects a pump unit (not shown) to the first pressure chamber 22. The pump unit (not shown) is operable to create a pressure differential from the atmospheric pressure in the first pressure chamber 22, as will be described hereinafter. The pump unit (not shown) is conventional and so no further description of the pump unit will be given herein.

The compartment 19 is in fluid communication with the throat 15 of the funnel 11 such that the breast receiving recess 16 forms part of the second pressure chamber 23. An outlet (not shown) extends from the second pressure chamber 23 to the milk receiving vessel (not shown) to define the fluid passageway. A valve (not shown) is disposed in the outlet (not shown) to seal the breast receiving recess 16 from an atmospheric pressure in the receiving vessel (not shown) when a pressure differential is formed in the second chamber 23, as will be explained hereinafter.

The compartment 19 comprises a first section 24 and a second section 25. The first section 24 is cylindrical and has an inner surface 26, and the second section 25 is cylindrical, with a smaller diameter than the first section 24, and has an inner surface 27. The throat 15 of the funnel 11 extends from an end face 28 of the second section 25.

The actuator 20 comprises a first piston element 30 and a second piston element 32. The first piston element 30 comprises inner and outer faces 33,34 and a circumferentially extending rim 35 which extends between the two faces 33,34. Similarly, the second piston element 32 comprises inner and outer faces 36,37 and a circumferentially extending rim 38 which extends between the two faces. The first and second piston elements 32 of the actuator 20 are connected or integrally formed with each other by a connecting member 39 which extends between the inner faces 33,36 of the first and second piston elements 30,32.

The first piston element 30 has an o-ring 40 extending circumferentially around its rim 35 which locates against and slidably seals with the inner surface 26 of the compartment first section 24, and the second piston element 32 has an o-ring 42 extending circumferentially around its rim 38 which locates against and slidably seals with the inner surface 27 of the compartment second section 25. The first pressure chamber 22 is defined between the inner faces 33,36 of the first and second piston elements 30,32.

Operation of the first embodiment of a breast pump will now be described with reference to FIGS. 2 and 3. A user inserts a breast 17 into the breast receiving recess 16 formed by the funnel 11 and locates the breast 17 against the inner surface 13 of the funnel 11 to form an air-tight seal. The actuator 20 is initially disposed in the compartment 19 in a neutral position, as shown in FIG. 2, with the second piston element 32 of the actuator 20 located proximate to the end face 28 of the compartment second section 25. The first and second pressure chambers are initially at an atmospheric pressure.

The user then operates the pump unit (not shown) to generate a positive pressure differential in the first pressure chamber 22. The pump unit (not shown) is a positive pressure pump unit and is fluidly connected to the first pressure chamber 22 by the inlet 21. Therefore, when the pump unit (not shown) is operated, the air pressure in the first pressure chamber increases and is sealed by the o-rings 40,42 extending around the first and second piston elements 30,32 of the actuator 20 so that the pump unit increases the air pressure in the first pressure chamber 22. Therefore, a positive pressure differential from the atmospheric pressure is generated in said first pressure chamber 22.

As the air pressure in the first pressure chamber 22 increases, the actuator 20 is urged to slide in the compartment 19 of the main body 12 because the inner face 33 of the first piston element 30 of the actuator 20 has a greater surface area than the inner face 36 of the second piston element 32 and so the resulting force acting on the first piston element 30 is greater than the force acting on the second piston element 32. Therefore, the actuator 20 is urged to move in the direction of the second piston element 32 from a neutral position to a refracted position such that the outer face 37 of the second piston element 32 is urged away from the end face 28 of the compartment second section 25.

When the actuator 20 slides in the compartment 19 to a retracted position, due to the positive pressure generated in the first pressure chamber 22, the volume of the second pressure chamber 23 increases, as shown in FIG. 3. The pressure in the second pressure chamber 23, including the breast receiving recess 16 defined by the funnel 11 therefore reduces as the actuator 20 slides such that a negative pressure is generated in the breast receiving recess 16 and said negative pressure is imparted on the user's breast 17 disposed therein. The negative pressure generated in the second pressure chamber 23 is proportional to the positive pressure generated in the first pressure chamber 22.

To return the actuator 20 to its neutral position from its retracted position, the positive pressure in the first pressure chamber 22 is released, so that the pressure differential in the first pressure chamber 22 is reduced and the actuator 20 is urged to slide from its refracted position to its neutral position due to the negative pressure differential in the second pressure chamber 23 acting on the actuator 20. As the actuator slides towards its neutral position the pressure generated in the second pressure chamber is increased towards atmospheric. The pump unit then acts in a cyclical manner to repeatedly increase and reduce the pressure in the first pressure chamber 22 so that a cyclical negative pressure acts on the user's breast 17 disposed in the breast receiving recess 16.

The vacuum created acts on the user's nipple to encourage milk expression from the user's nipple which then flows from the breast receiving recess 16 along the fluid passageway defined by the main body 12 to the milk receiving vessel (not shown). The user continues to operate the pump unit (not shown) until the desired quantity of milk has been expressed. The user then removes the breast pump 10 from the breast 17.

Although in the above embodiment the actuator 20 comprises first and second piston elements 30,32 connected by a connecting member 39, it will be appreciated that in an alternative arrangement the connecting member 39 forms the second piston element 32, such that the o-ring 42 perpendicularly extends around the connecting member 39 and slidably locates against the inner surface 27 of the second section 25 of the compartment 19.

Figure 4:
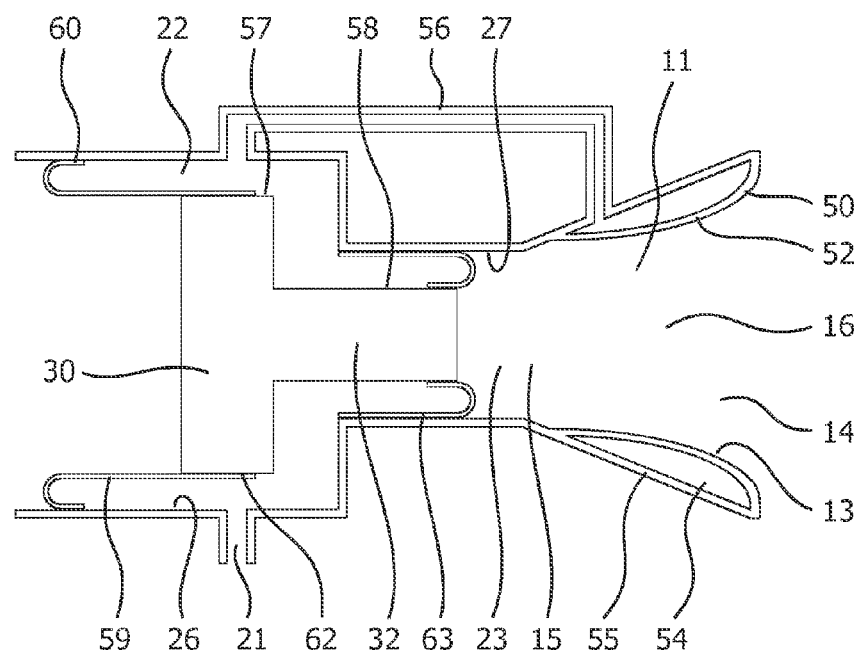
FIG. 4 shows a schematic cross-sectional view of a second embodiment of a breast pump.
Figure 5:
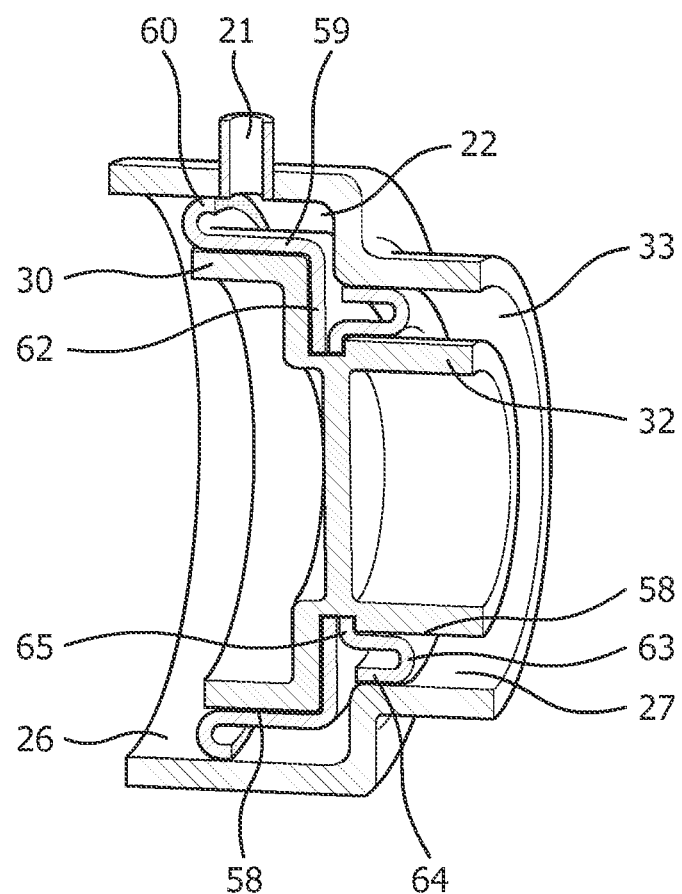
FIG. 5 shows a perspective cross-sectional view of the breast pump shown in FIG. 4.
Figure 6:
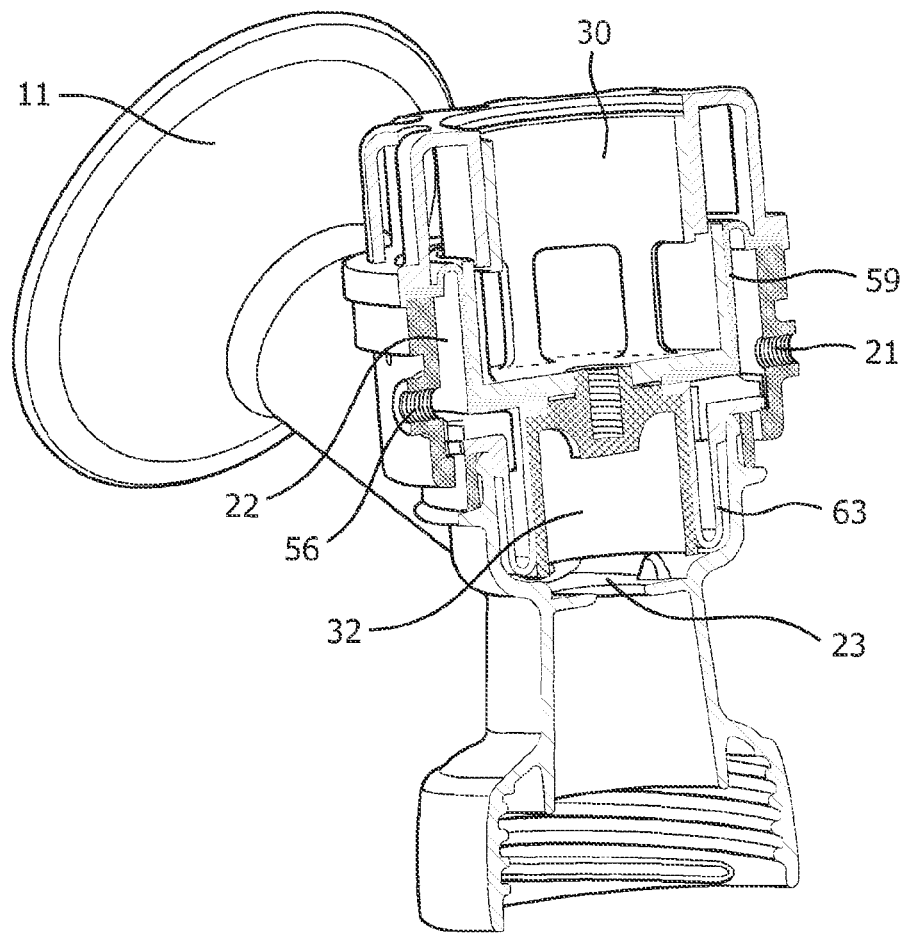
FIG. 6 shows another perspective cross-sectional view of the breast pump shown in FIG. 4.

Referring now to FIGS. 4 to 6, a second embodiment of a breast pump is schematically shown. The breast pump shown in FIG. 4 has the same general arrangement and features as the breast pump shown in the first embodiment described above, and so a detailed description will be omitted herein. Furthermore, features and components corresponding to features and components described above will retain the same reference numerals.

The second embodiment of a breast pump has an insert 50 disposed in the mouth 13 of the funnel 11. The insert 50 has a circle symmetric flexible, deformable wall 52 extending around an inner portion of the mouth 13 of the funnel 11 from an outer end 53 to proximate, or into, the throat 15 of the funnel 11. An inner face of the wall 52 forms the inner surface 13 of the funnel 11 against which a user's breast locates, and a cavity 54 is defined between the wall 52 and a funnel wall 55. The wall 52 is deformable into the breast receiving recess 16 during use to apply a compressive force to the nipple and/or areola in an attempt to aid the expression of milk from the breast, as will be explained hereinafter.

A pressure conduit 56 fluidly connects the cavity 54 to the first pressure chamber 22 so that the pressure generated in the first pressure chamber 22 is generated in the cavity 54.

The actuator 20 comprises a first piston element 30 and a connecting member which in this embodiment forms a second piston element 32. The actuator 20 is disposed in the compartment 19 such that the first piston element 30 is disposed in the compartment first section 24, and the second piston element 32 extends from the first piston element 30 into the compartment second section 25.

The first piston element 30 is cylindrical with a circumferentially extending rim 57 and the second piston element 32 is cylindrical with a circumferentially extending rim 58. A first circumferentially extending rolling seal 59 extends from the rim 57 of the first piston element 30 to the inner surface 26 of the compartment first section 24. An outer edge 60 of the first rolling seal 59 is folded back on itself and is fixedly mounted to the inner surface 26 of the compartment first section 24. The first rolling seal 59 extends to the rim 57 of the first piston element 30 and is fixedly mounted thereto at an inner edge 62. Therefore, the first rolling seal 59 forms an airtight seal between the first piston element 30 and the inner surface 26 of the compartment first section 24, and is foldable over itself so that the actuator 20 can slide in the compartment 19, as will become apparent hereinafter.

Similarly, a second circumferentially extending rolling seal 63 extends from the rim 58 of the second piston element 32 to the inner surface 27 of the compartment second section 25. An outer edge 64 of the second rolling seal 63 is fixedly mounted to the inner surface 27 of the compartment second section 25. The second rolling seal 63 extends to the rim 58 of the second piston element 32 and an inner edge 65 is folded back on itself and is fixedly mounted thereto. Therefore, the second rolling seal 63 forms an airtight seal between the second piston element 32 and the inner surface 27 of the compartment second section 25, and is foldable over itself so that the actuator 20 can slide in the compartment 19, as will become apparent hereinafter.

An advantage of using rolling seals is that the life time of the seal is increased compared to other sealing arrangements, and the membrane of the rolling seals maintains an airtight seal.

The first pressure chamber 22 is defined between the first and second rolling seals 59,63, and the second pressure chamber 23 extends from the second rolling seal 63 to the mouth 14 of the funnel 11. An outlet (not shown) extends from the second pressure chamber 23 to the milk receiving vessel (not shown) to define the fluid passageway. A valve (not shown) is disposed in the outlet (not shown) to seal the breast receiving recess 16 from an atmospheric pressure in the receiving vessel (not shown) when a pressure differential is formed in the second chamber 23

Operation of the second embodiment of a breast pump will now be described with reference to FIGS. 4 to 6. A user inserts a breast (not shown) into the breast receiving recess 16 formed by the funnel 11 and locates the breast against the inner surface 13 of the funnel 11 defined by the inner face of the insert deformable wall 52 to form an air-tight seal. The actuator 20 is initially disposed in the compartment 19 in a neutral position, as shown in FIG. 4, wherein there is atmospheric pressure in each pressure chamber. The first and second pressure chambers 22,23 are initially at an atmospheric pressure.

The user then operates the pump unit (not shown) to generate a positive pressure differential in the first pressure chamber 22. The pump unit (not shown) is a positive pressure pump unit and is fluidly connected to the first pressure chamber 22 by the inlet 21. Therefore, when the pump unit (not shown) is operated, the air pressure in the first pressure chamber increases and the first pressure chamber 22 is sealed by the first and second rolling seals 59,63 extending around the first and second piston elements 30,32 of the actuator 20 so that the pump unit increases the air pressure in the first pressure chamber 22. Therefore, a positive pressure differential from the atmospheric pressure is generated in said first pressure chamber 22.

A positive pressure differential from the atmospheric pressure is also generated in the cavity 54 of the insert 50 by means of the pressure conduit 56 fluidly connecting the cavity 54 to the first pressure chamber 22.

As the air pressure in the first pressure chamber 22 increases, the actuator 20 is urged to slide in the compartment 19 of the main body 12 due to the increased pressure acting on the first piston element 30 of the actuator 20. Therefore, the actuator 20 is urged to move in the direction of the second piston element 32 from a neutral position to a retracted position. The first and second rolling seals 59,63 each roll over themselves so that a pressure seal is maintained.

When the positive pressure generated in the first pressure chamber 22 causes the actuator 20 to slide in the compartment 19 to a retracted position, the volume of the second pressure chamber 23 increases. The pressure in the second pressure chamber 23, including the breast receiving recess 16 defined by the funnel 11 therefore reduces as the actuator 20 slides from its neutral position such that a negative pressure is generated in the breast receiving recess 16 and said negative pressure is imparted on the user's breast disposed therein. The negative pressure generated in the second pressure chamber 23 is proportional to the positive pressure generated in the first pressure chamber 22. The positive pressure differential generated in the first pressure chamber 22 is also generated in the cavity 54, which causes the deformable wall 52 of the insert 50 to deform inwardly into the breast receiving recess 16 and therefore urge against the user's breast.

To return the actuator 20 to its neutral position from its retracted position, the positive pressure in the first pressure chamber 22 is released, so that the pressure differential in the first pressure chamber 22 is reduced and the actuator 20 is urged to slide from its refracted position to its neutral position due to the negative pressure differential in the second pressure chamber 23 acting on the actuator 20. As the actuator 20 slides towards its neutral position the pressure generated in the second pressure chamber is increased towards atmospheric. Further, the deformable wall 52 of the insert 50 deflates. The pump unit then acts in a cyclical manner to repeatedly increase and reduce the pressure in the first pressure chamber 22 so that a cyclical negative pressure acts on the user's breast disposed in the breast receiving recess 16, and the insert 50 cyclically massages the breast.

Each rolling seal 59,63 is formed from a molded or casted resilient material and, in the present embodiment, each rolling seal 59,63 is molded, or cast, in the desired shape that each seal has when the actuator 20 is in a neutral position, as shown in FIG. 4.

Therefore, the elasticity force of the rolling seals 59,63 caused by the deformation of each seal 59,63 when the actuator 20 is urged to move due to an increased pressure in the first pressure chamber 22 act as a restoring force to urge the actuator 20 to return to the neutral position when the pressure differential in the first pressure chamber is released.

An advantage of the above arrangement is that the actuator 20 is urged to return to its neutral position independent of the pressure differential in each of the pressure chambers 22,23, for example when the user's breast is removed from the funnel 11, or the pump unit (not shown) is detached from the inlet 21.

The vacuum created acts on the user's nipple to encourage milk expression from the user's nipple which then flows from the breast receiving recess 16 along the fluid passageway defined by the main body 12 to the milk receiving vessel (not shown). The user continues to operate the pump unit (not shown) until the desired quantity of milk has been expressed. The user then removes the breast pump 10 from the breast.

One advantage of the above arrangement is that it enables both a positive and negative pressure differential to be generated using a single pump unit which is operated to generate a positive pressure differential.

Although in the above embodiment rolling seals are shown and described, it will be appreciated that the insert arrangement may be used with a sliding seal arrangement as described in the first embodiment. Similarly, it will be appreciated sliding seal arrangement may be used without an insert.

Although in the above embodiments the first and second piston elements are cylindrical and the corresponding first and second sections of the compartment are also cylindrical, it will be appreciated that the embodiments are not limited thereto and may have alternative arrangements.

An advantage of the above arrangements is that the pump unit may be used to create a positive pressure in the first chamber, such that a negative pressure is generated in the second chamber and therefore at a user's breast. Therefore, milk expressed from a user's breast is not urged to be drawn into the pumping mechanism by the pump unit generating a negative pressure and so increases the hygiene of the breast pump, and eliminates a need to clean and/or sterilize the pump mechanism.

Although in the above described embodiments the compartment 19 defining first and second pressure chambers 22,23 is disposed in the main body, it will be appreciated that the compartment 19 may be disposed distal to the main body, for example in the throat of the breast pump, or mounted to the main body of the breast pump.

Although in the present embodiments the pump unit is configured to generate a positive pressure differential from atmospheric, it will be appreciated that in an alternative arrangement the pump unit generates a negative pressure differential from atmospheric in the first chamber such that a positive pressure differential is generated in the second chamber.

Although in the present embodiments the funnel is integrally formed with the main body of the breast pump, it will be understood that in an alternative embodiment the funnel is removably mounted thereto for ease of sterilizing and cleaning.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived there from.

The invention claimed is:

1. A breast pump comprising a first pressure chamber, a second pressure chamber and an actuator disposed to fluidly divide the two chambers, wherein the actuator is movable to generate an inverse pressure differential in the second chamber when a pressure differential is generated in the first pressure chamber, or a pressure differential is released from the first pressure chamber, wherein the actuator comprises a first piston element and a second piston element, and wherein the first pressure chamber is disposed between the first piston element and the second piston element.

2. A breast pump according to claim 1, further comprising a breast receiving funnel, wherein the second pressure chamber includes a breast receiving recess defined by the funnel.

3. A breast pump according to claim 1, further comprising a compartment, wherein the actuator is slidably disposed in the compartment.

4. A breast pump according to claim 3, wherein the first and second piston elements each comprise a seal extending from an outer rim of each piston element to an inner surface of the compartment to form a fluid seal.

5. A breast pump according to claim 4, wherein the seal is a rolling seal.

6. A breast pump according to claim 4, wherein the first pressure chamber is disposed between the seal of the first piston element and the seal of the second piston element.

7. A breast pump according to claim 4, wherein the second pressure chamber extends from the seal of the second piston element.

8. A breast pump according to claim 1, wherein the second piston element extends from the first piston element.

9. A breast pump according to claim 1, further comprising an inflatable insert disposed in the breast receiving funnel for massaging a user's breast disposed therein, and a pressure conduit which fluidly communicates the insert with the first pressure chamber, such that the insert inflates when a positive pressure differential is generated in the first pressure chamber.

10. A breast pump according to claim 1, further comprising a pump unit for generating a pressure differential in the first pressure chamber.

\* \* \* \* \*